United States Patent [19]

Rincoe

[11] Patent Number: 5,062,855
[45] Date of Patent: Nov. 5, 1991

[54] ARTIFICAL LIMB WITH MOVEMENT CONTROLLED BY REVERSING ELECTROMAGNET POLARITY

[76] Inventor: Richard G. Rincoe, 49 S. Holman Way, Golden, Colo. 80401

[21] Appl. No.: 262,287

[22] Filed: Oct. 25, 1988

Related U.S. Application Data

[63] Continuation-in-part of Ser. No. 102,162, Sep. 28, 1987, abandoned.

[51] Int. Cl.$^5$ .......................... A61F 2/54; A61F 2/70
[52] U.S. Cl. ....................................... 623/24; 623/64;
 414/1; 901/40; 901/36
[58] Field of Search ...................... 401/46, 38–40, 401/36, 21, 30; 623/24–25, 57–65; 414/1, 2, 4–5, 7

[56] References Cited

U.S. PATENT DOCUMENTS

| | | | |
|---|---|---|---|
| 3,449,768 | 6/1969 | Doyle | 623/24 |
| 3,751,733 | 8/1973 | Fletcher et al. | 623/24 |
| 4,246,661 | 1/1981 | Pinson | 901/36 |
| 4,302,138 | 11/1981 | Zarudianshy | 623/24 |
| 4,414,984 | 11/1983 | Zarudianshy | 901/46 |
| 4,770,662 | 9/1988 | Giampapa | 623/24 |
| 4,792,338 | 12/1988 | Rennerfelt | 623/57 |
| 4,853,630 | 8/1989 | Houston | 901/46 X |

FOREIGN PATENT DOCUMENTS

| | | | |
|---|---|---|---|
| 0245391 | 5/1987 | German Democratic Rep. | 901/40 |
| 0562669 | 6/1975 | Switzerland | 414/4 |
| 0721324 | 3/1980 | U.S.S.R. | 901/40 |
| 0747715 | 7/1980 | U.S.S.R. | 414/4 |
| 1134362 | 1/1985 | U.S.S.R. | 901/36 |
| 1140945 | 2/1985 | U.S.S.R. | 901/40 |
| 1161374 | 6/1985 | U.S.S.R. | 901/36 |
| 1585262 | 2/1981 | United Kingdom | 901/36 |

*Primary Examiner*—Randall L. Green
*Assistant Examiner*—David H. Willse
*Attorney, Agent, or Firm*—Donald W. Margolis

[57] ABSTRACT

A material handling system in the form of a grappling device or of a robotic or prosthetic limb is provided which can function for performing work. The system includes a plurality of magnets including at least one electromagnet. In preferred embodiments the magnets are hinged together at opposite ends and disposed inside a sheath. By reversing the polarity of selected electromagnets in the limb, the limb or an associated material handling device can be moved from an open position to a closed position for gripping an object. In turn, by again reversing the polarity of the electromagnets, the object can be released and the limb returned to an open position. The limb may be in the form of an anatomical hand, an arm or a foot, and the resilient casing may take the form and appearance of an artificial skin. The outer skin may be a glove with the inside of the glove having electrical conductors deposited thereon with contacts engaging opposite ends of the selected magnets. A power source is connected to the conductors for reversing the polarity of the magnets.

10 Claims, 5 Drawing Sheets

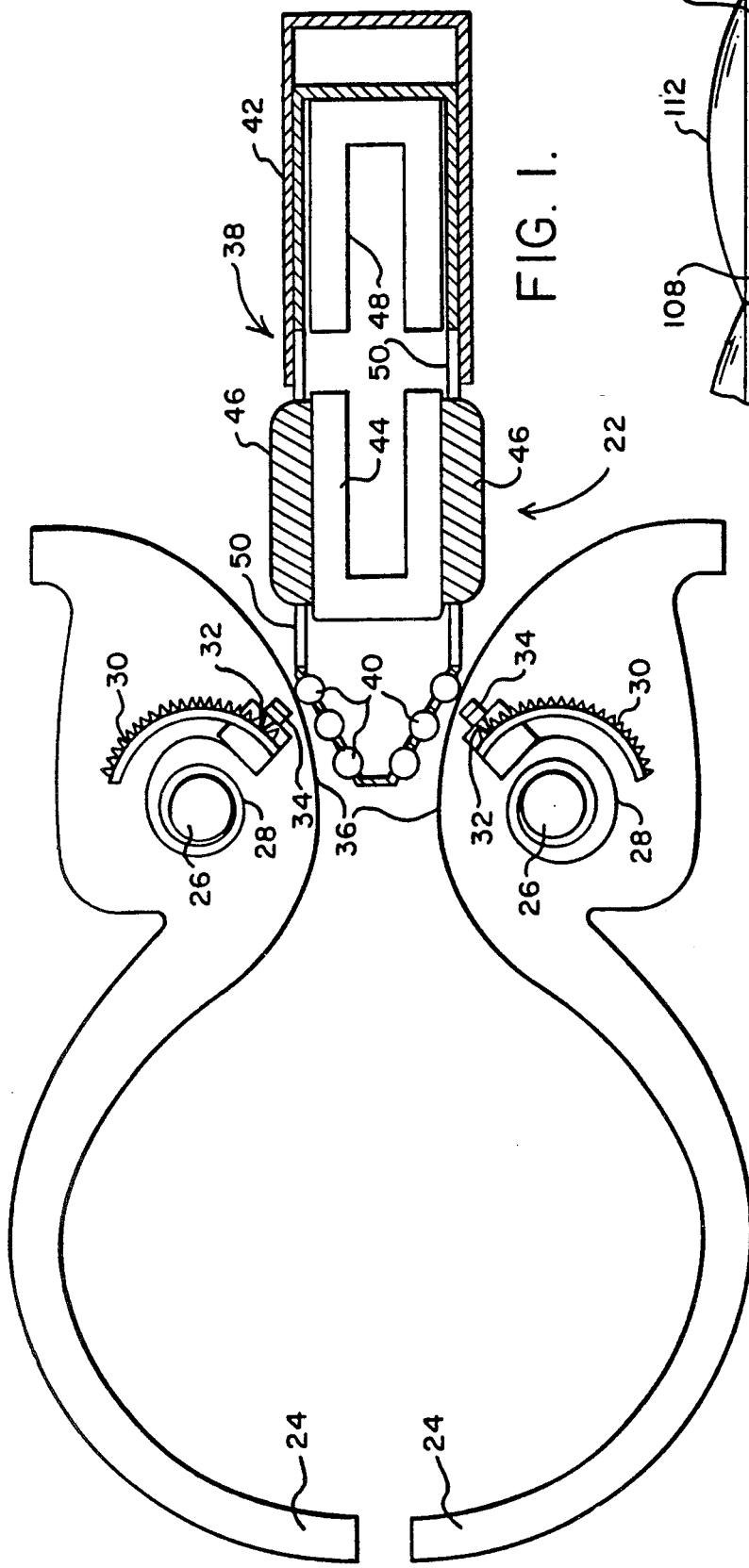
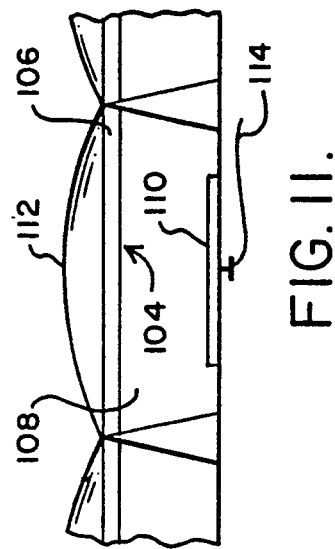
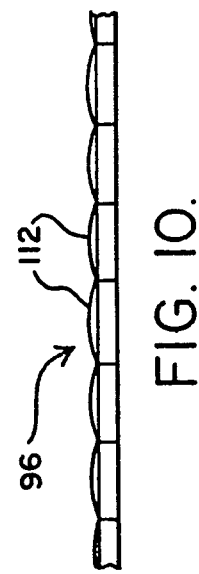

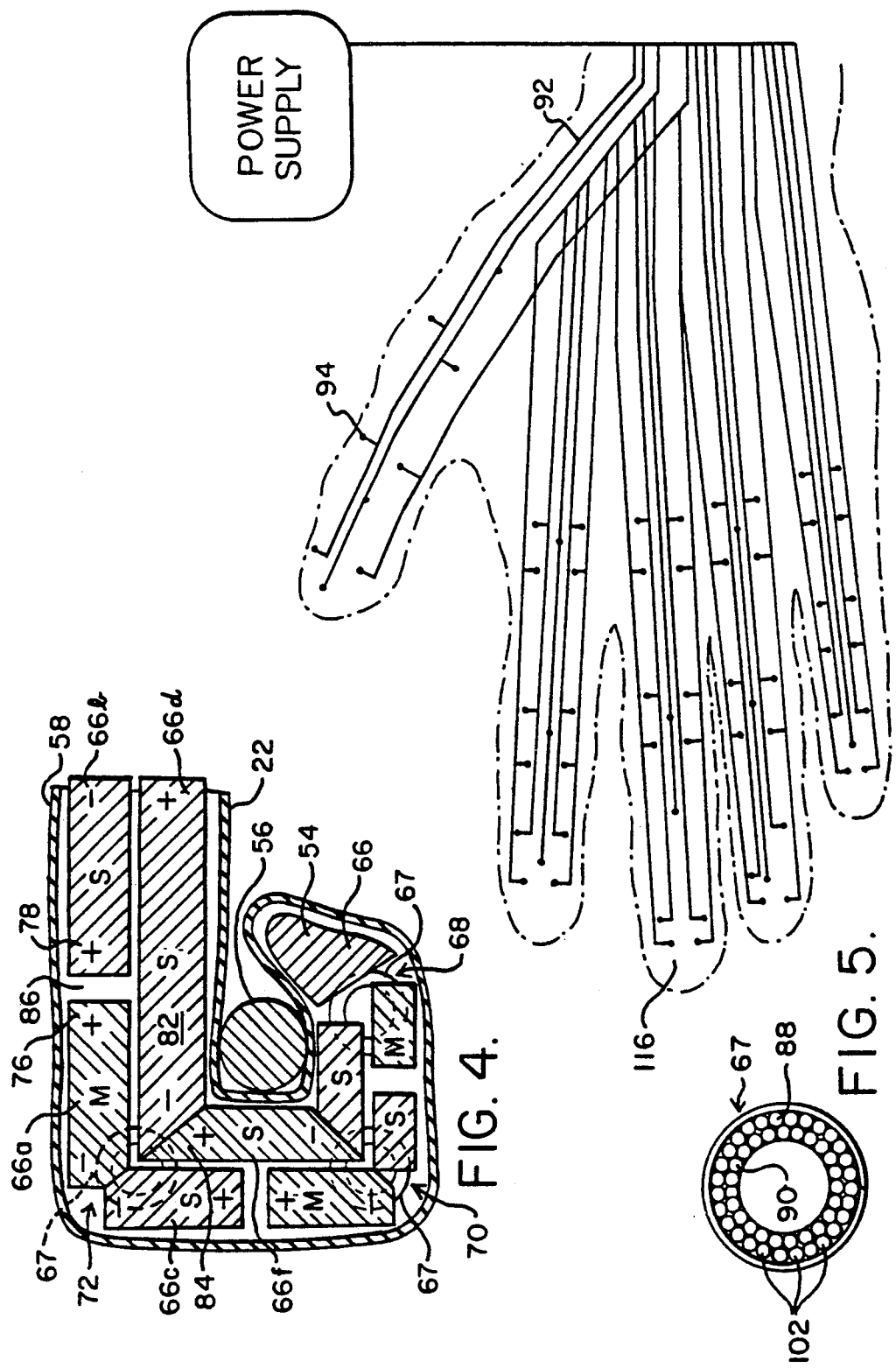

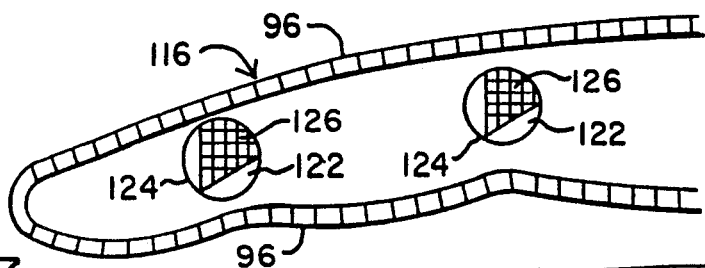
FIG. 7.
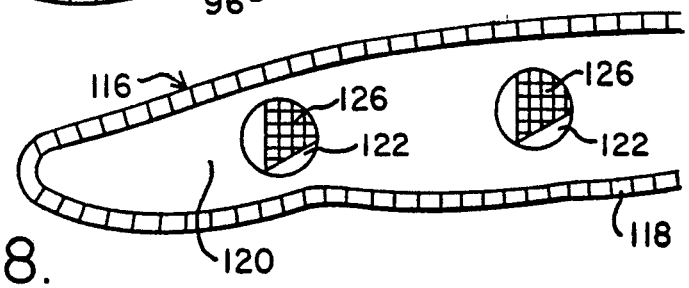
FIG. 8.
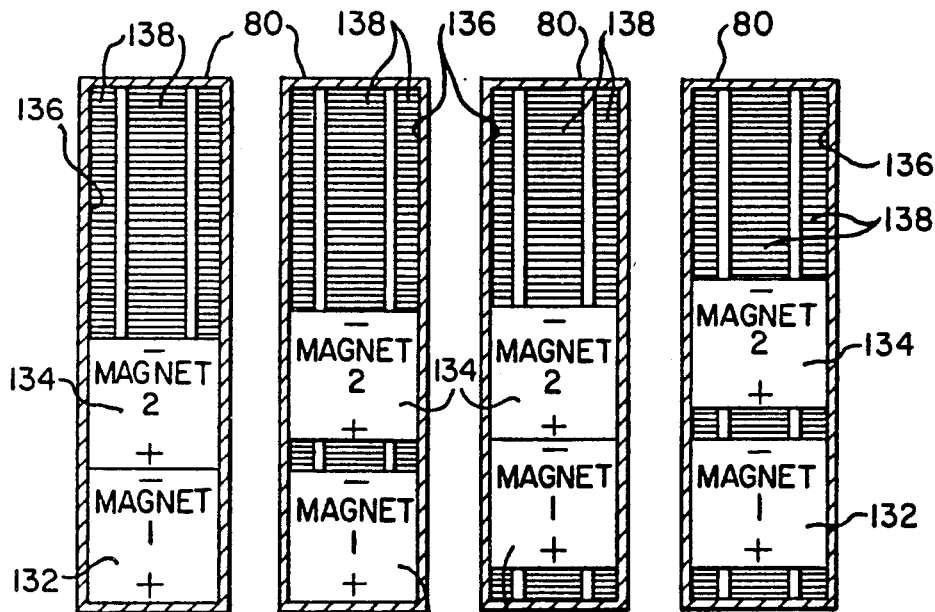
FIGS. 13A. 13B. 13C. 13D.
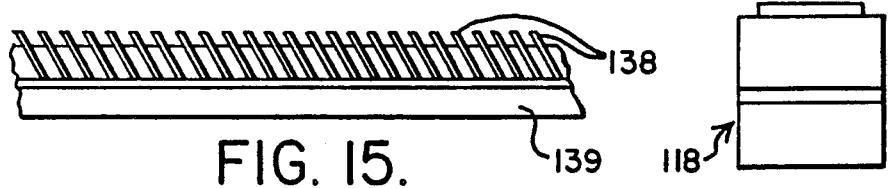
FIG. 15.
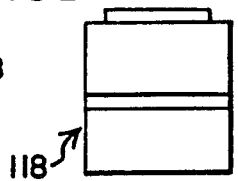
FIG. 12.

ARTIFICAL LIMB WITH MOVEMENT CONTROLLED BY REVERSING ELECTROMAGNET POLARITY

RELATED APPLICATIONS

This application for patent is a continuation-in-part of U.S. Pat. Application Ser. No. 102,162 filed on Sept. 28, 1987 entitled "Rincoe Limb" by Richard J. Rincoe, now abandoned.

FIELD OF THE INVENTION

The present invention relates broadly to the field of material handling grapples including magnet control elements. It also relates to such grapples in the form of article manipulators which are analogous with a human hand and which are capable of human arm type movement. More particularly, but not by way of limitation, it relates to a robot arm motion controller drive system, and to such a robot arm having a gripping jaw. In certain applications the system may be used as a prosthetic, device, such as a hand, an arm, a foot or a leg.

DISCUSSION OF THE PRIOR ART

Heretofore there have been a variety of different types of mechanical hands. An example of a digitally-controlled artificial hand is described in Douglas U.S. Pat. 4,643,473. Zarudiansky U. S. Pat. 4,302,138 describes a remote handling device wherein a "slave hand" is controlled by a "master hand" in the form of a glove which receives the hand of an operator. The artificial hand of this latter reference is also responsive to a plurality of sensors, and is useful for handling objects in a dangerous environment. Duderstadt U. S. Pat. 3,820,168 discloses a system which utilizes a servomotor for operating a prosthetic limb. The servomotor is actuated by a controller which responds to local variations in a user's muscular rigidity as determined by one or more pressure sensors bearing upon the flesh of the wearer of the prosthetic limb.

None of the above-mentioned references disclose the unique features and novel structure of the grapple, robotic limb or prosthetic device of the present invention as described herein. Furthermore, none of the above-mentioned patents disclose the use of pairs of magnets or electromagnetic components to initiate or to control the motion of a grapple, of a robotic limb, or of a prosthetic device.

SUMMARY OF THE INVENTION

A principal object of the present invention is to provide a completely new and different grapple or robotic limb which can be operated at various speeds and at locations remote from the operator, or as a prosthetic device, all using magnets or electromagnets for operating the movement of the device.

Another object of the present invention is to provide a completely new and different magnetic and electromagnet method of operating a grapple, a robotic limb or a prosthetic device.

Another object is to provide a grapple, a robotic limb or a prosthetic device which is modular in design, and which can therefore be provided in interchangeable sizes, and in various strengths.

Still another object of the invention is to provide grapples, robotic limbs or prosthetic devices which have the ability to perform both delicate work and powerful work.

The present invention provides grapple devices in the form of article manipulators The grapples may be analogous with a limb, such as a human arm, hand, foot or leg, and having movement characteristics which may simulate the movement of such a limb. The devices may also be in the form of a robotic limb, such as a hand, arm, foot or leg which can function anatomically as a prosthetic device, or as a robot or a part of a robot in performing robotic tasks.

Each limb and grapple which is produced in accordance with the teaching of the present invention includes a plurality of magnets and/or electromagnets The magnets and/or electromagnets may be of various lengths. Where a joint is required, the ends of the magnets which are located in adjacent portions of the device may be flexibly hinged together to form a joint. In certain embodiments the magnets may be disposed inside a flexible resilient sheath. Where the device simulates a prosthetic device the resilient sheath may simulate an artificial outer skin. Where the device is in the form of a hand, the outer skin may be in the form of a glove. Whether in the form of a glove, or not, the inside of the skin or of the glove or other form of sheathing may have electrical conductors deposited thereon which include contacts which are positioned to engage contacts on adjacent electromagnets in the system. A direct current (d.c.) power source is provided for connection to the electromagnets. As described in greater detail below, the selective actuation or reversal of the polarity of the d.c. current to an electromagnet can cause an attraction or a repulsion between adjacent magnets. Where conductors are present in the sheathing they can be used to make the contacts which are necessary for actuating or reversing magnetic polarity in the electromagnets.

By reversing the polarity of selected magnets in a grapple, or of a robotic limb, or of a prosthetic device which includes a plurality of magnets, the entire device or a selected portion can be moved. For example, a grapple can be moved from an open position to a closed position for gripping an object, or a prosthetic device can be moved to perform work or move a user. In turn, by again reversing the polarity of the magnets, a grasped object can be released, or a prosthetic device returned to its original position.

In the formation of joints for systems of the present invention, magnets which are adjacent to the joint area may be flexibly connected together in a number of ways. For example, the ends of a pair of adjacent magnets can themselves be connected together at their adjacent ends using a hinge. One preferred form of a hinge may be of a ball bearing disk-shaped type, as described in further detail below. Such a hinge is almost frictionless, and in view of the fact that the magnets of the present invention move substantially silently in an electromagnetic field, the operation of the system can be both smooth and quiet.

In all embodiments of the present invention the sheath, skin or glove which surrounds the system can include sending sensors which are electrically connected to receiving sensors at an operator's station, perhaps for example, covering an operator's glove. The sensors can be used for sensing both touch and squeeze of the grappling device, robotic limb or prosthetic device. Additionally, temperature sensors can be added to the sheath for measuring hot and cold conditions.

In yet another embodiment of the present invention, microsize photoelectric cells in arrays can be attached to one side of each joint in the system. In such a system, as a joint is opened certain photoelectric cells are activated, while when a joint is closed other photoelectric cells are activated. Matching arrays at the operator's work station are electrically connected to the arrays on the joints. They in turn can be used to drive the magnet field of the electromagnets in the system to open or close a portion of the system, and also to provide microfine movement thereof.

These and other objects of the present invention will become apparent to those skilled in the art from the following detailed description, showing the contemplated novel construction, combination, and elements as herein described, and more particularly defined by the appended claims, it being understood that changes in the precise embodiments of the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view, partially in cross-section for the sake of clarity, of a material handling grappling clamp, according to the present invention;

FIG. 4 is a sectional side view, partially in phantom, of the finger of the robotic limb shown in FIG. 3, and showing the internal details of the electromagnets and joints in a closed position grasping an object;

FIG. 5 is an enlarged sectional side elevational view of a bearing of the type which can be used as a joint in the devices of the present invention;

FIG. 6 illustrates a top view, partially in phantom, of a glove used as an outer skin or sheath for a robotic limb or finger of the type shown in FIGS. 2-4 and showing the electrical conductors carried therein;

FIG. 7 schematically illustrates a matrix of sensors covering portions of the exterior of a finger according to the present invention;

FIG. 8 schematically illustrates a matrix of sensors covering portions of the interior of a finger of an operator's glove, which portions correspond to the matrix of sensors on the exterior of the finger of FIG. 7, and of a series of pressure sensors which are carried in the skin of the operator's glove;

FIGS. 9 and 10 illustrate an enlarged top and side view, respectively, of one form of sensor shown in FIGS. 7 and 8, which sensor may be used on the exterior of the robotic limb for sensing touch and squeeze;

FIG. 11 is a further enlarged side view of one of the sensors shown in FIGS. 9 and 10;

FIG. 12 is a further enlarged side view of one of the pressure sensors shown in FIG. 8; 5 FIGS. 13A-13D illustrates schematically in a series the detail of the use of magnets, according to the teaching of the present invention, as a mechanical push rod, which is useful, for example, for movement of large components, such as a robotic or prosthetic arm or leg, and which includes directional fins for controlling the direction of movement of the magnets;

FIG. 15 shows a side cross-sectional view taken along line 15—15 of the fins shown in FIG. 14;

DESCRIPTION OF THE PREFERRED EMBODIMENT

Figure 9:
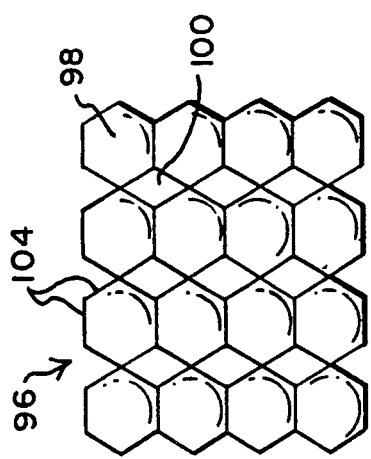

In the following illustrations like numerals have been used to designate the same or similar components throughout the several drawing figures.

Referring to FIG. 1, there is shown a top elevational view, partially in section for the sake of clarity, of a material handling grappling clamp system, generally 22, produced in accordance with the present invention. Clamp system 22 consists of a pair of mirror image claw members 24, each of which is pivotally mounted on a pivot 26. While not required for the operation or explanation of the present invention, each pivot mount 26 and claw component 24 may be normally urged into an open or a closed position. For example, in the embodiment shown a spring 28 is associated with each claw 24 and pivot 26 in a manner such that each claw member 24 is normally urged apart from one another into an open unclamped configuration. Similarly, in the embodiment shown each claw element 24 is shown to include a curved ratchet slot 30 and an associated pawl 32 which operates as a braking mechanism. Either or both pawl braking mechanisms 32 can be released from associated ratchet 30 by release element 34, to thereby allow claw 24 to move under the pressure of spring 28 towards its normally open position. In preferred embodiments, and in keeping with the philosophy of the present invention, release element 34 may be a magnetic couple of the type described in greater detail below.

The inner surface 36 of each claw element 24 is in the form of a cam. Magnetic drive mechanism 38 terminates in rolling members 40 which are located in following contact with both cam surfaces 36. As can be seen, as rolling members 40 are moved to the left towards the claw members 24 rolling members 40 are caused to bear against cam surfaces 36 and urge claws 24 into an closed position. It has previously been noted that the selective release of pawl braking mechanism 32 by release element 34 causes claws 24 to be urged open by springs 28. This combination of features allows claws 24 of clamp 22 to be selectively opened and closed by the action of magnetic drive 38 or of pawl braking mechanism 32, respectively.

Magnetic drive mechanism 38, which is at the heart of the present invention, is constructed and operates as follows. Magnetic drive mechanism 38 includes a sheath 42 which surrounds and supports a fixed U-shaped electromagnet or permanent magnet 44. Fixed magnet 44 carries a pair of fins 46 which extend through and are attached to sheath 42 to thereby secure magnet 44 against movement. A second U-shaped magnet, electromagnet 48 is slidably mounted within sheath 42 for movement toward and away from claws members 24. Electromagnet 48 carries drive element 50 which is tapered at its distal end. As shown, the tapered distal end of drive element 50 carries rolling members 40. As indicated in FIG. 1, drive element 50 is slotted, thus allowing it to ride past, and yet be oriented and guided by fins 46.

As is well known, magnets of opposite polarity attract one another and magnets of the same polarity repel one another. In operation, second movable U-shaped electromagnet 48 may be electrically activated so that its two poles are both the same as the adjacent poles of fixed U-shaped magnet 44. This will result in electromagnet 48 being repelled from fixed magnet 44, and thus fixed magnet 48 and roller members 40 attached to drive element 50 will be moved away from cam surfaces 36 of claw elements 24, thus allowing them to be urged into a more open position by springs 28. In another mode of operation, second movable U-shaped electromagnet 48 may be electrically activated so that its poles are both of different polarity to the adjacent poles of fixed U-shaped magnet 44. This will result in electromagnet 48 being attracted towards fixed magnet 44. Thus fixed magnet 48 and roller members 40 attached to drive element 50 will be moved towards cam surfaces 36 of claw elements 24, thus urging the claws into a more closed position by overcoming the opening forces of springs 28. It is thus seen that electromagnet 48 and attached drive element 50 is capable of moving towards and away from fixed magnet 44 as the polarity of second magnet 48 is modified. The removal of electromagnetic energy from electromagnet 48 will cause the magnets to return to a neutral position and urge claws 24 towards their normally open position.

In the system shown in FIG. 1 the selective activation of release element 34 will cause pawl braking mechanism 32 to selectively release or engage ratchet 30, to thus further control the closing movement of claws 24. Thus, in preferred embodiments, if the passive ratchet braking system is used, as illustrated, no electricity is necessary to hold claws 24 in position. To optimize the strength of this system, the magnets will normally be caused to draw together to cause motion, such as closing of an element. As is known, as the magnets become closer together their mutual magnetic attraction increases. By reversing the ratchet, pawl and spring elements, and the curvature of the contact surfaces, the clamp can be provided in a manner such that it will require magnetic power to bring it into a closed, clamping position. Furthermore, fixed magnet 44 may also be a reversible electromagnet, in which case magnet 48 may be either a permanent magnet or an electromagnet.

Elements of the system which are adjacent to or in proximity to magnet or electromagnetic portions of the system will generally be composed of non-magnetic or non-ferromagnetic materials, which include, but are not limited to plastic, wood and wood products, paper and paper products, ceramics, and many common metals and alloys such as aluminum, brass, copper, tin and the like.

Figure 2:
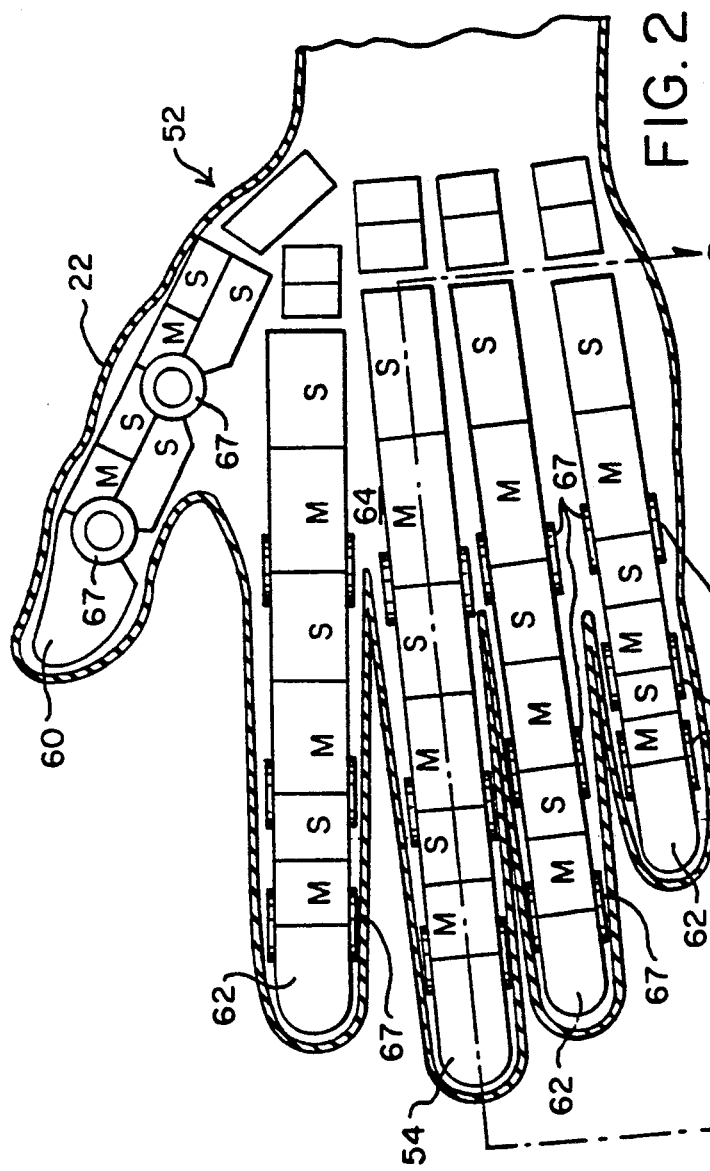
FIG. 2 schematically illustrates, partially in cross-section, a top view of a robotic limb or of a human hand prosthetic device.
Figure 3:
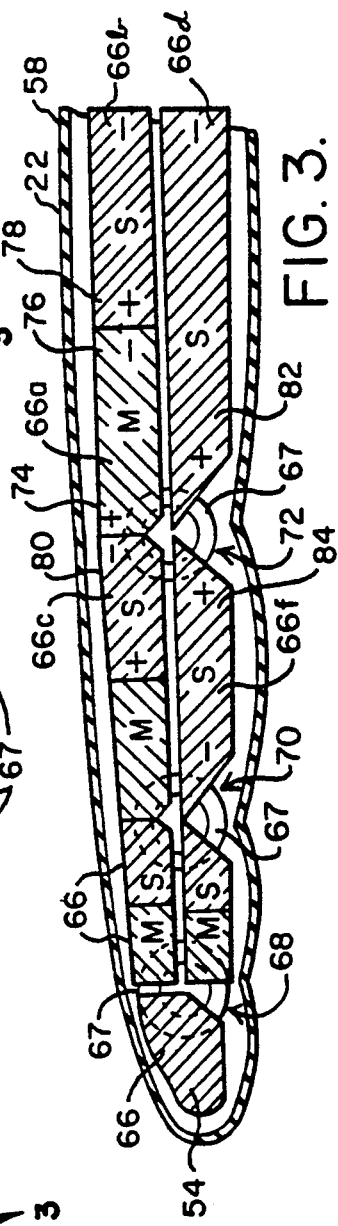
FIG. 3 is an enlarged cross-sectional side view, partially in phantom, of the index finger of the limb shown in and taken along line 3—3 of FIG. 2, and showing the internal details and relationships of the magnets and joints of the finger in an open, extended position.

Another form and embodiment of the present invention is set forth in FIG. 2, which schematically illustrates, partially in cross-section, a top view of a robotic limb or of a human hand prosthetic device, generally 52. Associated FIG. 3 is an enlarged cross-sectional side view, partially in phantom, of the index finger 54 of limb 52 shown in and taken along line 3—3 of FIG. 2, and showing the internal details and relationships of the magnets and joints of the finger in an open, extended position; while FIG. 4 is a sectional side view, partially in phantom, of finger 54 of limb 52, showing the internal details of the electromagnets and joints in a closed position grasping an object 56. While limb 52 is depicted as a human hand, it should be kept in mind during the following discussion and exposition of the present invention the details, principles and operations apply as well to an arm, foot or leg which can function anatomically and perform a desired task, or to a purely mechanical material handling device, such as described and discussed with respect to FIG. 1, and other mechanical embodiments. The limb 52 includes a flexible resilient artificial outer skin such as a glove 58. Glove 58 is made up of a thumb 60, index finger 54, three other fingers 62, and a palm 64. Inside of glove 58 are a plurality of elongated electromagnets 66a–66f having north poles indicated as positive (+) and south poles indicated as negative (−) at opposite ends of each magnet 66. The magnets 66 preferably have cores made of rare earth alloys which provide extremely strong magnetic characteristics, but may be of any magnetic or electromagnetically activatable material. Magnets 66 are shaped, tempered, and, in use are electrically activated by a d.c. power source so that the polarity of selected magnets can be switched as desired during the operation of the limb 52. The ends of adjacent magnets 66 which are disposed in a joint area of the limb 52 are joined by a low friction double ball bearing race, toroid-shaped hinge 67 shown in greater detail in FIGS. 5, 19 and 20.

In FIG. 2 a top plan view of limb 52 is shown with the thumb 60, index finger 54, fingers 62, and a portion of the palm 64 made up of a plurality of magnets 66 inside the glove 58. Some of the magnets 66 are marked by the capital letter "M" meaning that such a magnet is moveable away from an adjacent magnet. Stationary (non-movable) magnets are indicated by the capital letter "S". The movement of M magnets 66 can be more clearly seen in FIG. 3 and FIG. 4.

In FIG. 3 a side view of index finger 54 is shown in an extended open position. Note from left to right the finger 62 includes a first joint 68, a second joint 70, and a third joint 72. The three joints 68, 70, and 72 use hinges 67 for joining together the ends of adjacent magnets 66, thus allowing the magnets 66 to pivot thereabout when the finger 62 is moved to a closed position shown in FIG. 4.

A more detailed discussion of the movement and operation of third joint 72 follows, it being understood that the first and second joints 68 and 70, as well as any other joint of this type in a limb or structure of this type will operate similarly. Referring to FIG. 3, an upper moveable magnet 66a is attached to hinge 67 of joint 72 with, in this open position, a left end 74 of the magnet 66a having a +pole and a right end 76 having a pole. Note a lower portion of the left end 74 is beveled at a 45° angle. A stationary upper magnet 66b, to the right of the magnet 66a, has a left end 78 with a +pole. The left end 78 of magnet 66b is disposed against the right end 767 of magnet 66a. Another stationary upper magnet 66c, to the left of the magnet 66a, has a right end 80 attached to the hinge 67. The right end 80 has a −pole. Note the lower portion of the right end 80 of magnet 66c is also beveled at a 45° angle.

A lower magnet 66d is disposed bellow the magnets 66a and 66b and has a left end 38 beveled at a 45° angle. The left end 82 is attached to the hinge 67 and has a −pole. Another lower magnet 66f is disposed below magnet 66c and has a right end 884 also beveled at a 45° angle and attached to the hinge 67. The right end 84 of magnet 66f has a +pole.

Referring now too FIG. 4 and further discussing the operation of finger 62 of limb 52, it can be seen that the finger 622 has now moved downwardly to grip a cylindrical shaft 56. The shaft 56 is illustrated in cross section. The shaft 56 is shown merely as an example of a work piece. The polarity of the magnet 66a has been changed as shown in FIG. 4. This has been accomplished by using an external source of electricity using electrical conductors and contacts of the type described in detail with regard to FIG. 6, below.

When the polarity of the magnets 66a and 66d is changed, the right end 76 of magnet 66a is repelled by the left end 78 of the magnet 66b, and accordingly the magnet 66a, which is moveable, begins to move to the left. A space 86 or gap is formed as shown in FIG. 4. At the same time, the right end 80 of magnet 66c is also repelled by the left end 74 of the magnet 66b. The magnet 66c is not free to move, but it is able to pivot downwardly on hinge 67 at an angle of 90°. The lower bevel of the right end 80 of magnet 66c now engages the lower bevel of the left end 74 of magnet 66a.

To enhance the movement of the third joint 72, the polarity of the magnet 66d has also been changed as shown in FIG. 4. While the repelling of the upper magnets 66a, 66b, and 66c is going on, the right end 84 of the magnet 66f is now attracted to the left end 82 of magnet 66d. The left end 82 has changed from + to −. The greater surface of the bevels of the right end 84 and the left end 82 aid in a more positive gripping force between the two magnets 66d and 66f.

When it is desired to release shaft 56 the polarities of the magnets 66a and 66d are again reversed to the polarities shown in FIG. 3 and the finger 62 moves upwardly returning to its open and extended position.

Thumb 60 in FIG. 2 illustrates a pair of lower magnets 66 which are hinged together and disposed adjacent to and below a plurality of both stationary and moveable upper magnets 66.

Figure 20:
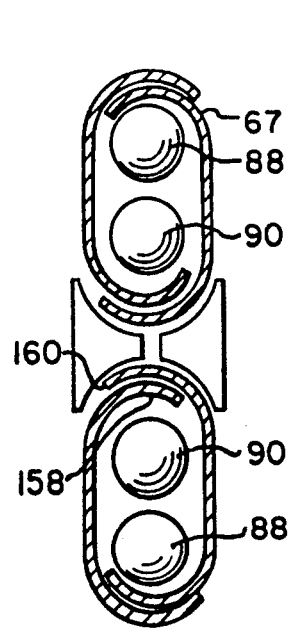
FIG. 20 shows a side cross-sectional view taken along line 20—20 of FIG. 19 of a hinge in relation to the locking system of FIGS. 16-19.
Figure 19:
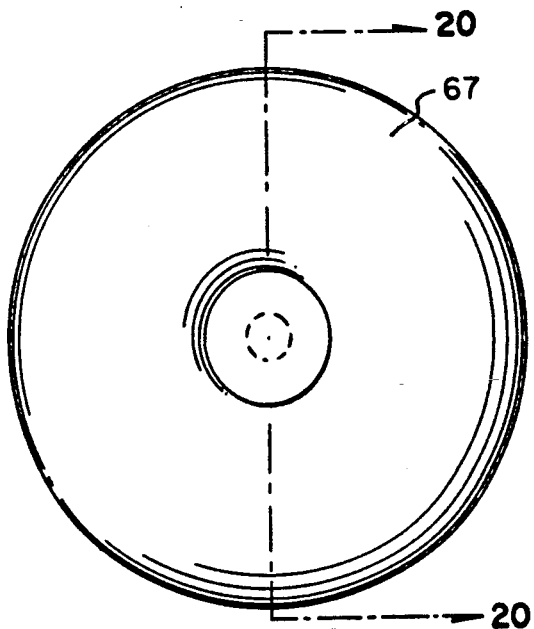
FIG. 19 shows a side elevational view of a hinge in relation to the system of FIGS. 16-18 for normally keeping the joints locked in an open or closed position.

FIGS. 5, 19 and 20 show enlarged views of toroid-shaped hinge 67. Hinge 67 is shown in phantom in FIGS. 3 and 4 to allow for improved clarity in illustrating the structure located in joints 68, 70, and 72. Hinge 67 as shown in FIGS. 5 and 20 includes an outer race 88, an inner race 90, and a plurality of roller ball bearings 102 disposed therebetween. Hinge 67 can be made of various sizes depending on the size and shape of the joint used in the limb. Other joints may be substituted for that which is illustrated.

In FIG. 6 glove 116 with leads 92 and contacts 94 illustrates one example of a means for applying the necessary selected electrical charges of the correct polarity to the magnets 66. A glove of this type or another form of sheath which carries conductors and contacts is useful as it eliminates individual electrical wires, soldering, and potential broken contacts. Such a glove 116, as illustrated, may be produced by turning the glove inside-out, suitably masking the glove to expose the desired conductor and contact pattern, and then coating it with electrical conductor material using any art known coating process, as for example vapor deposition. When the process is completed and the mask removed, the glove 116 will have the necessary conductor leads 92 and contacts 94 correctly positioned for applying electrical charges to a desired magnet. After such deposition the glove 116 is inspected and turned inside-in.

While the outside electrical source for powering and switching the electromagnets is not shown in the drawings, it can be any commonly available direct current source such as a battery, a rectified a.c. current, or the like. Also parallel wound conductive coils on the magnets can be used for reversing a magnet's polarity. The use of such windings will allow greater amounts of power to be applied to the magnet for longer periods of time.

It should be noted here that in a remote environment a limb 52 can be interchangeable with different types of limbs, and can be used in different size scales. For example, for large powerful work the limb 52 can be made larger and of a different shape. When an operator moves his hand 2 inches the limb can be made to move 4, 12, or 24 inches depending on how the limb is calibrated. In the converse the limb 52 can be designed to operate on a smaller scale for handling small objects and delicate instruments. In such a scaled down operation, when the operator moves his hand 2 inches, the limb will respond by moving perhaps only ½ or ¼ inch. This ratio control is important in a remote presence situation where only one robot is provided to perform different types of tasks.

FIG. 9 and FIG. 10 illustrate a top and side view of a honeycomb structure 96 made up of a plurality of intermixed touch sensors 98 having a hexagonal shape and squeeze sensors 100 having a diamond shape. This may be produced, for example by vapor deposition coating of the inside top of each wall 104 of the sensors 98 and 100 with an electrical conductor 106. One of the walls 104 is shown enlarged in FIG. 11 with the conductor 106 at the top thereof. The inside of a chamber 108 of each sensor 98 and 100 is filled with a fluid, not shown, that changes its electrical conductivity with a contact 110 located at the bottom of chamber 108. When a slight bulge 112 of the liquid or gas is depressed a change in resistance of the electrical impulse from the top to the bottom of the chamber 108 is metered via an electric lead 114 connected to the contact 110.

The metered valve from lead 114 is digitized using methods well known in the art, and using telemetry techniques the valve signal may be transmitted to a remote operator (not shown), wearing an operator glove 116, one finger of which is shown in FIG. 8. The glove 116 contains a plurality of magnetically-operated pins 118 corresponding to the touch and squeeze sensors 98 and 100 making up the honeycomb structure 96. The honeycomb structure 96 surrounds the exterior surface of limb finger 62 shown in FIG. 7. The digitized valve is decoded and an impulse is transmitted to the operator's glove 116 via the lead 114, and the corresponding pin 118 presses onto an operator's finger 120. One of the magnetic pins 118 is shown enlarged in FIG. 12. It can be appreciated that many of these pins 118 working together will substantially duplicate the sense of touch to the operator wearing the glove.

It has been found that the six-sided bubbles 112 in the touch sensors 98 will extend out farther than the four-sided or diamond-shaped bubbles 112 of the squeeze sensors 100. Surface tension causes this phenomenon. Therefore, when the diamond-shaped bubbles are depressed, a hinge locking mechanism (not shown) in the operator's glove 116 begins to stiffen. The more the diamond-shaped surfaces or bubbles 112 are compressed, the more the operator's glove 116 will stiffen, thus restricting movement and hence duplicating the sensation of squeeze.

As shown in FIG. 7, limb finger 62 is covered with sensors 96 which serve as "sending sensors," and the operator's glove 116 shown in FIG. 8 which is also covered with sensors 122 which serve as "receiving sensors". The sensors 96 and 122 are very thin and can be as plentiful as the application and operation of the limb 52 warrants.

Also shown in FIG. 7 and FIG. 8 are small disks 124 added to the outside of each hinge 67 as shown in FIGS. 2, 3 and 4. The disks 124 include a matrix of micro size photoelectric cells 126 mounted therein. Each disk 124 is attached to one side of each hinge 67. Disposed on the other side of the hinge 67 and not shown in the drawings is an aperture disk with an oriented opening in it. As the hinge 67 moves, different photoelectric cells 126 are activated by light passing through the oriented opening and others deactivated as they are removed from the light. A matching photoelectric disk 124 and aperture (not shown) on the operator's glove 116 helps drive the magnetic field of the magnets 66 in the finger 62. When the disks 124 of the finger 62 line up with the disks 124 on the operator's glove 116 the motion of the finger 62 stops. Since there can be many photoelectric cells in each disk 124, microfine motion can be detected and duplicated. This allows for small and delicate work using the limb 52.

It can be appreciated while touch and squeeze sensors 98 and 100 are discussed above, temperature sensors can also be applied to the glove 116 equally well for measuring temperature. Further, through the use of binocular television the glove operator can enhance his motion and sense of depth duplication of limb 52

Figure 14:
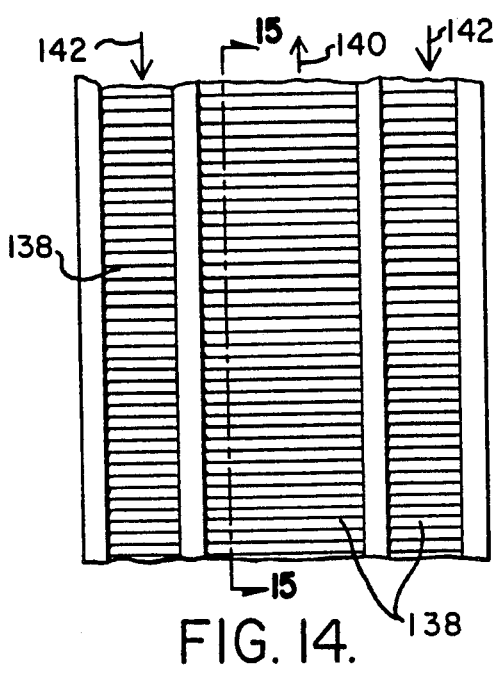
FIG. 14 shows an enlarged front plan view of the small fins shown in FIGS. 13A-13D, and which allow movement of the magnets in only one direction.

Additional embodiments of the present invention are now described and illustrated in FIGS. 13-15. In the above drawings the limb 52 is depicted as a hand with fingers 62. When moving larger limbs such as an arm or a leg, a push rod or piston 130 may be desirable for extension and retraction of the limb. In FIGS. 13A-13D the piston 130 uses a first magnet 132 and a second magnet 134. The first magnet 132 has a constant polarity of −at the top and +at the bottom. The second magnet 134 can change polarity repeatedly using, for example, an outside electrical power source similar to those discussed above. When the second magnet 134 is +on the bottom it draws the first magnet toward it. As soon as the two magnets touch, the polarity of the second magnet 134 is changed and it repels itself up a cylinder 136 having fins 138. When it stops the polarity is again changed and the second magnet 134 draws the first magnet 132 upwards toward it. This sequence is illustrated by the series shown from left to right in FIGS. 13A-13D. This process is repeated over and over until both magnets 132 and 134 move up the cylinder 136. When the magnets are pushing a limb having a substantial mass, the process is repeated faster and more often, to make use of the strength of the magnetic field over a short distance.

FIGS. 12 and 13 illustrate a front and side view of small steel fins 138 laid out like fish scales. The fins allow the magnets 132 and 134 to move in only one direction at a time. Arrow 140 represents movement in an upward direction and arrows 142 represents movement in a downward direction. When it is time for the magnets 132 and 134 to change direction, the fins 138 are retracted and reversed by magnets 139 so that they face in an opposite direction. The process is then repeated, but in an opposite direction, as in the retraction of the limb.

Figure 16:
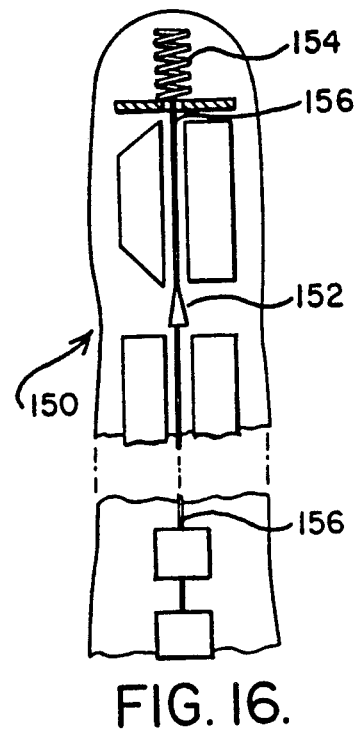
FIG. 16 is a side view of a finger of a robotic limb of the type shown in FIG. 3, and diagrammatically showing some the internal details of a system for normally keeping the joints locked in an open or closed position.
Figure 17:
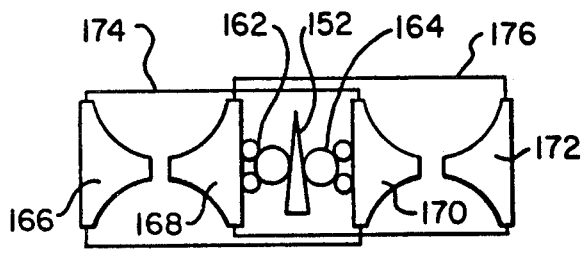
FIGS. 17 and 18 provide an enlarged side view and top view, respectively, of the locking mechanism of FIG. 16, and diagrammatically showing some the additional internal details of one system for normally keeping a hinge at a joint locked in an open or closed position.
Figure 18:
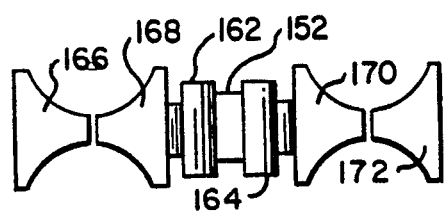

Now referring to FIGS. 16-20 a system and components are provided for use in locking a modified finger 150 or other limb in an open or closed position. FIG. 16 provides a side view, similar to that of a finger or other limb of the type shown in FIG. 3. FIG. 16 also diagrammatically shows some of the internal relational details of a wedge 152 which can be used for normally keeping finger 150 locked in an open or closed position. FIGS. 17 and 18 provide and diagrammatically show additional internal details of an enlarged side view and top view, respectively, of the locking mechanism of FIG. 16, which is one system for normally keeping the finger 150 locked in an open or closed position. Now, referring again to FIG. 16, finger 150 includes groupings of fixed and movable magnets of the type described with regard to FIGS. 2, 3 and 4. However, this limb has been modified to locate spring 154, or other biasing means, at the end or fingertip of finger 150 or of any other limb or probe embodying the present invention. Spring 154 normally urges wire 156 and attached wedge 152 towards the end of finger 150. Now, attention is directed to FIG. 19 which provides a further enlarged side elevational view of hinge 67 in relation to the hinge locking system of FIGS. 16-18. FIG. 20 shows a side cross-sectional view taken along line 20—20 of FIG. 19 of such a hinge 67 in relation to the locking system of FIGS. 16-18. As now revealed in FIG. 20, hinge 67 is closed at its inner radial surface by a pair of overlapping ends 158 and 160. As will be detailed below, when overlapping ends 158 and 160 are squeezed together by the hinge locking system of FIGS. 16-18, hinge 67 is immobilized.

As previously noted, spring 154 urges wedge 152 towards the end of finger 150. Now referring to FIGS. 17 and 18, when wedge 152 is urged towards the end of finger 150 it exerts pressure against roller sets 162 and 164. A first locking brake mechanism 166 and 168 in the shape of a toroidal hub for hinge 67, and a second locking brake mechanism 170 and 172, also in the shape of a toroidal hub for a hinge is included. Portion 166 of first locking brake mechanism and portion 172 of second locking brake mechanism are interconnected by tie rods 174. Also, portion 168 of first locking brake mechanism and portion 170 of second locking brake mechanism are interconnected by tie rods 176. Now in operation, when wedge 152 is urged against roller sets 162 and 164, and roller 162 causes both portion 168 of the first locking brake mechanism and portion 170 of the second locking brake mechanism to move outwardly away from wedge 152. However, as a result of the outward movement of portions 168 and 170, tie rods 174 and 176 cause both portion 166 of the first locking brake mechanism and portion 172 of the second locking brake mechanism to move inwardly toward wedge 152. This in turn results in first locking brake mechanism 166 and 168 and second locking brake mechanism 170 and 172 to squeeze hinge 67, with the result that overlapping ends 158 and 160 come together and immobilize the hinge which in turn locks the finger 150. The two small rollers shown in roller sets 162 and 164 are useful in reducing friction within the system.

It will now be noted that wire 156 extends backwardly from wedge 152 to movable magnet 180 which is associated with electromagnet 182. When electromagnet 182 is activated it attracts and moves magnet 180 away from the end of the finger 150, thus counteracting the pull of spring 154, causing wedge 152 to release pressure from rollers 162 and 164 and frees hinges 167 for movement. When electromagnet 182 is deactivated it again allows wedge 152 to be pressed against roller sets 162 and 164 to thus once more lock the hinges into position. By utilizing such a spring powered locking mechanism, the constant use of electromagnetic force is not required to lock a system into a desired position. Therefore, in the system the electromagnetic force is activated only when the hinges are to be released. The force and power of the magnets assist in keeping all of the elements in alignment.

If an always released system is desired the position and location of spring 154 and magnets 180 and 182 could be reversed, or the orientation of wedge 152 could be reversed.

The grapples or robotic limbs of the present invention can easily be used to handle hazardous waste, defuse bombs, repair satellites in space, along with many other work functions.

It is clear that the present invention is well adapted to carry out the objects and to attain the ends and advantages mentioned herein as well as those inherent in the invention. While the invention has been particularly shown, described and illustrated in detail with reference to preferred embodiments and modifications thereof, it should be understood by those skilled in the art that the foregoing and other modifications are exemplary only, and that equivalent changes in form and detail may be made therein without departing from the true spirit and scope of the invention as claimed, except as precluded by the prior art.

The embodiments of the invention for which an exclusive privilege and property right is claimed are defined as follows:

1. A robotic or prosthetic limb such as a hand, arm, foot, or leg, or a portion of such a limb which can be moved to function in a substantially anatomical manner, said limb comprising inn combination:
    an outer skin;
    at least two magnets including at least one electromagnet, each said magnet having a first end and a second end, each said first end of each magnet carrying or capable of carrying a first magnetic polarity and each said second end of each magnet carrying or capable of carrying a second magnetic polarity, each said magnet being linearly aligned in a manner such that one pole end of each magnet is adjacent to only one pole end of each next adjacent magnet, said magnets being disposed inside said outer skin in a first position, each said electromagnet being located and positioned within said skin inn a manner such that when it is activated its magnetic field will affect each adjacent magnet;
    means for pivotally attaching at least one pole end of one said electromagnet to only one pole end of an adjacent magnet by a hinge, said hinge being disposed in a joint area of the limb, wherein at least one said magnet is moveable;
    an electrical power source connected to each said electromagnet; and
    means for activating or switching the polarity of at least one said electromagnet, whereby the activating or switching of the polarity of said electromagnet causes either the switched electromagnet or one of said magnets which is adjacent to said switched electromagnet to move from a first position to a second position to thereby cause controllable movement of said limb or a portion of said limb.

2. The robotic or prosthetic limb of claim wherein said outer skin moves from said first position to a second position when the polarity of said electromagnet is changed.

3. The limb as described in claim 2 wherein the first position is an open extended position of the limb and the second position is a closed gripping position of the limb.

4. The limb as described in claim 1 wherein the first position is an open extended position of the limb and the second position is a closed gripping position of the limb.

5. The limb as described in claim 1 wherein the outer skin is a glove.

6. The limb as described in claim 5 wherein the inside surface of the glove includes electrical conductors with contacts deposited thereon, said contacts disposed and located to engage said electromagnets, the electrical conductors connected to said electrical power source.

7. A robotic or prosthetic limb such as a hand, arm, foot or leg which can function anatomically for performing work, the limb comprising:
    a flexible resilient artificial outer skin in the form of a glove, said glove carrying on the inside surface thereof electrical conductors with contacts;
    a plurality of linearly aligned adjacent electromagnets, each said electromagnet having a first end capable of carrying a first magnetic polarity and a second end capable of carrying a second magnetic polarity, one end of each said electromagnet being pivotally attached to the adjacent end of each adjacent electromagnet and disposed inside said glove in a first position, wherein said pivotal attachments use ball-bearing, toroid-shaped hinges, said hinges being disposed in a joint area of the limb; and
    an electrical power source connected to the conductors for changing polarity of one or moore selected electromagnet, the changing of the polarity causing said electromagnet and said glove to move from a first position to a second position.

8. The limb as described in claim 7 wherein said hinges further include disks attached to the sides thereof, said disks including photoelectric cells for sensing microfine movement of the limb.

9. The limb as described in claim 7 wherein an outer surface of the glove is covered with sensors for sensing touch and squeeze.

10. The limb as described in claim 9 wherein the sensors are in the form of a thin honeycomb structure having an electrical conductive fluid therein, said fluid changing in conductivity when the limb is exposed to touch and squeeze.

* * * * *